US007144418B1

(12) United States Patent  (10) Patent No.: US 7,144,418 B1
Lennox  (45) Date of Patent: Dec. 5, 2006

(54) METHOD, AND SYSTEM FOR SELECTIVE CEREBRAL HYPOTHERMIA

(75) Inventor: Charles D. Lennox, Hudson, NH (US)

(73) Assignee: MedCool, Inc., Westwood, MA (US)

( * ) Notice: Subject to any disclaimer, the term of this patent is extended or adjusted under 35 U.S.C. 154(b) by 298 days.

(21) Appl. No.: 10/285,165

(22) Filed: Oct. 31, 2002

Related U.S. Application Data

(60) Provisional application No. 60/335,177, filed on Nov. 2, 2001.

(51) Int. Cl.
A61F 7/00 (2006.01)
(52) U.S. Cl. ....................................... 607/105; 607/106
(58) Field of Classification Search ............. 606/20–27; 607/96–114
See application file for complete search history.

(56) References Cited

U.S. PATENT DOCUMENTS

| 4,904,237 | A |   | 2/1990  | Janese ........................... 604/28 |
| 5,342,301 | A | * | 8/1994  | Saab ........................ 604/103.13 |
| 5,486,208 | A | * | 1/1996  | Ginsburg ..................... 607/106 |
| 5,837,003 | A | * | 11/1998 | Ginsburg ..................... 607/106 |
| 5,971,979 | A | * | 10/1999 | Joye et al. ..................... 606/21 |
| 6,217,552 | B1 |   | 4/2001  | Barbut et al. .............. 604/113 |
| 6,409,747 | B1 | * | 6/2002  | Gobin et al. ................ 607/113 |
| 6,432,102 | B1 |   | 8/2002  | Joye et al. ..................... 606/21 |
| 6,623,514 | B1 |   | 9/2003  | Chin ........................... 607/105 |
| 6,648,878 | B1 | * | 11/2003 | Lafontaine ................... 606/21 |
| 6,656,209 | B1 | * | 12/2003 | Ginsburg ..................... 607/106 |
| 6,660,026 | B1 |   | 12/2003 | Larnard et al. ............. 607/104 |
| 6,682,508 | B1 | * | 1/2004  | Meythaler et al. .......... 604/246 |
| 6,692,519 | B1 | * | 2/2004  | Hayes, Jr. ................... 607/105 |
| 6,699,269 | B1 | * | 3/2004  | Khanna ....................... 607/105 |
| 2002/0198579 | A1 |   | 12/2002 | Khanna ....................... 607/105 |
| 2004/0143312 | A1 | * | 7/2004  | Samson et al. ............. 607/105 |

OTHER PUBLICATIONS

Piepgras, et al., "Rapid Active Internal Core Cooling for Induction of Moderate Hyperthermia in Head Injury by Use of an Extracorporeal Heat Exchanger", Neurosurgery Online, Feb. 1998, vol. 42, No. 2. http://www.neurosurgery-online.com. Visited Nov. 24, 2003.
Alsius, A New Degree of Care, The Fortius Catheter, http://www.alsius.com/us/fortius.htm. Visited Nov. 24, 2003.
Hachimi-Idrissi, et al., "Mild Hypothermia Induced by a Helmet Device: A Clinical Feasibility Study", Resuscitation 51:275 (2001).
Ommaya, et al., "Direct Extravascular Brain Cooling in the Normothermic Animal", Neurology 12:882 (1962).

(Continued)

*Primary Examiner*—Roy D. Gibson
(74) *Attorney, Agent, or Firm*—Thomas J. Engellenner; Charlton Shen; Nutter McClennen & Fish LLP (57) ABSTRACT

Disclosed is a method and system for inducing selective cerebral hypothermia. The system includes a brain cooling device, a body warming device, and a control console. Brain cooling is accomplished with a ventricle catheter where cold fluid is circulated within one or both lateral ventricles. Body heating is accomplished with a central venous catheter. By combining effective brain cooling with controlled body warming, hypothermia therapy can be applied selectively to the brain thereby avoiding the serious complications associated with whole body hypothermia therapy.

26 Claims, 6 Drawing Sheets

OTHER PUBLICATIONS

Tooley, et al., "Significant Selective Head Cooling can be Maintained Long-Term After Global Hypoxia Ischemia in Newborn Piglets", Pediatrics, vol. 109, No. 4, pp. 643-649, Apr. 2002.

Javid, et al., "Hypothermic Ventricular Perfusion: Evaluation of Use in Cerebrovascular Occlusion, New York State Journal of Medicine", pp. 248-251, Jan. 5, 1967.

Tooley, et al., "Head Cooling with Mild Systemic Hypothermia in Anesthetized Piglets is Neuroprotective", Annals of Neurology, vol. 53, No. 1, pp. 65-72, Jan. 2002.

White, M.D., "Cerebral Hypothermia and Circulatory Arrest: Review and Commentary", Mayo Clin. Proc. 53:450 (1978).

Costal, et al., "Experimental Production of Cerebral Hypothermia by Ventricular Perfusion Techniques", J. Neurosurg, 20:112 (1963).

* cited by examiner

METHOD, AND SYSTEM FOR SELECTIVE CEREBRAL HYPOTHERMIA

CROSS REFERENCE TO RELATED APPLICATIONS

This application is entitled to the benefit of provisional application Ser. No. 60/335,177 filed 2001, Nov. 2.

BACKGROUND

1. Field of Invention

This invention relates to a method, and system for inducing global cerebral hypothermia while maintaining normal core temperature for the prevention of secondary brain injury from stroke, trauma, or surgery.

2. Description of Prior Art

Patients suffering from stroke or head trauma, or have undergone invasive brain or vascular surgery are at risk from secondary brain injury. Secondary brain injury is a result of the innate healing response of the brain to the original insult caused by several not completely understood mechanisms. Regardless of the specific mechanisms involved, the end result is swelling of the brain caused by edema, which can lead to a critical or terminal rise in intra-cranial pressure.

It has long been known that hypothermia is neuroprotective. Hypothermia has a positive affect on all know mechanisms that lead to secondary brain injury. Hypothermia is routinely used during brain and other invasive surgeries to protect the brain from surgical interruptions in blood flow. Hypothermia has also been shown to be effective in controlling swelling of the brain in trauma and stroke patients.

The effectiveness of hypothermia is a function of depth and duration; the deeper the hypothermia, and/or the longer it is applied the more neuroprotective it is. However, hypothermia has historically been applied systemically, and the depth and duration of hypothermia is limited by the patient's ability to tolerate the therapy.

Systemic hypothermia has historically been accomplished by immersion of the patient's body in a cool bath. Today there are several commercial systemic hypothermia systems available. They consist of blankets or pads where cooled water is circulated through channels in the walls of the blanket or pad, and the patient's body is maintained in intimate contact. Medivan Corp. manufactures an example of a modern hypothermia system under the trade name Arctic Sun Cooling System.

Systemic hypothermia has been demonstrated to be effective in reducing secondary injury from stroke, trauma, and surgery however, there are several drawbacks to this approach: 1) It takes several hours to lower a patient's body to therapeutic temperatures. This delay in achieving therapeutic temperatures allows for the progression of irreversible secondary injury to the brain. 2) The practical therapeutic hypothermic temperature and duration is limited by the ability of the patient to tolerate, or survive the therapy. 3) The side effects of systemic hypothermia are frequent and can be life threatening, especially in frail patients. Side effects include shivering, cardiac arrhythmia and arrest, pneumonia, infections, and coagulation disorders. 4) The target of hypothermia therapy is the brain; therefore inducing hypothermia systemically places the patient at undue risk. 5) During the "critical phase" (rewarming period) of hypothermia treatment, there is no effective way to manage a sudden and critical increase in intra-cranial pressure, since re-cooling the body to reverse the increase in intra-cranial pressure takes several hours. 6) Systemic hypothermia poses significant clinical and logistical patient management issues.

There are several examples in the art where catheters are constructed with a cooling means, which is placed into the carotid artery to cool the blood entering the head. This offers an advantage over systemic hypothermia, since it provides a means to cool the head to lower temperatures than the rest of the body, but it still results in systemic hypothermia. Also, since the scientific evidence suggests that hypothermia must be maintained for extended periods of time, there is a great risk that clots will form on the catheters and migrate into the brain leading to episodes of stroke.

Barbut et al. (U.S. Pat. No. 6,217,552) suggests that cerebral hypothermia may be accomplished by placing a catheter in a lateral ventricle of the brain, and a second catheter into the subarachnoid space, and then pumping cooled fluid from the first catheter in the lateral ventricle to the second catheter in the subarachnoid space where the fluid flows from the lateral ventricle, through the third ventricle, and into the subarachnoid space via the cerebral aqueduct. This approach may be effective in inducing cerebral hypothermia in a normal healthy brain; brains that are suffering ischemia or trauma are often swollen. Swelling of the brain compresses the ventricles and cerebral aqueduct which prevents or limits fluid flow between the lateral ventricle, and the subarachnoid space. One significant problem with inducing cerebral hypothermia by cooling the cerebrospinal fluid in the ventricles is that it results in systemic hypothermia due to the fact that the brain is highly vascular, and that up to ⅓ of the body's heat is generated in the brain. Barut does not suggest a means of maintaining normal core temperature while inducing cerebral hypothermia by ventricle cooling.

Nowhere in the art is it suggested that directly cooling the walls of a ventricle of the brain may induce global cerebral hypothermia and therefore prevent secondary brain injury. Nowhere in the art is it suggested that cerebral hypothermia can be accomplished by removing the cerebrospinal fluid from a brain ventricle, then inflating a balloon within said ventricle, and then cooling the walls of said ventricle with said balloon. Nowhere in the art is a means taught for inducing cerebral hypothermia by ventricle cooling while maintaining normal core temperature.

SUMMARY

Therefore, it is an object of this invention to provide a method and apparatus for preventing secondary brain injury by inducing selective cerebral hypothermia. In accordance with one aspect of this invention, selective brain cooling is accomplished by placing a cooling device(s) into one or more ventricles of the brain and by placing a heating device into the central vascular system, then cooling said ventricle(s) with said cooling device(s) while simultaneously replacing the heat removed from the body by said cooling device(s) with said heating device. In accordance with another aspect of this invention, secondary brain injury is prevented by placement of a cooling balloon catheter into a lateral ventricle of the brain, then removing the cerebrospinal fluid within the lateral ventricle with said cooling balloon catheter, and then cooling the walls of the lateral ventricle with said cooling balloon catheter thereby cooling the brain. In accordance with another aspect of this invention, selective cerebral hypothermia is accomplished by placing a cooling balloon catheter into a lateral ventricle of the brain and a heating catheter into the central vascular system, then removing the cerebrospinal fluid within the lateral ventricle with said cooling balloon catheter, and then cooling the walls of the lateral ventricle with said cooling balloon catheter, where cooling is accomplished by circulating cold fluid through the balloon of said cooling balloon catheter, and simultaneously heating blood in the central vascular system with said heating catheter thereby replacing the heat removed from the body by the cooling balloon catheter. In accordance with another aspect of this invention, selective cerebral hypothermia is accomplished by placing a cooling device into one or more ventricle(s) of the brain and a heating balloon catheter into the central vascular system, then cooling said ventricle(s) with said cooling devices(s), while simultaneously heating blood in the central vascular system where said heating is accomplished by circulating heated fluid through the balloon of said heating balloon catheter thereby replacing the heat removed from the body by the ventricle cooling device(s). In accordance with another aspect of this invention, secondary brain injury is prevented by placement of a balloon catheter into a lateral ventricle of the brain, and a heating catheter into the central vascular system, then removing the cerebrospinal fluid within the lateral ventricle with said balloon catheter, and then cooling the walls of the lateral ventricle to a predetermined temperature for a predetermined time with said balloon catheter, and simultaneously heating blood in the central vascular system with said heating catheter thereby replacing the heat removed from the body by the cooling balloon catheter. In accordance with another aspect of this invention, secondary brain injury is prevented by placement of a balloon catheter into a lateral ventricle of the brain, then removing the cerebrospinal fluid within the lateral ventricle with said balloon catheter, and then cooling the walls of the lateral ventricle with said balloon catheter to a predetermined temperature where then the temperature is increased gradually over a period of time from the initial low temperature, with the period of time being greater than one hour and less than two months and simultaneously heating blood in the central vascular system with said heating catheter thereby replacing the heat removed from the body by said cooling balloon catheter. In accordance with another aspect of this invention, apparatus for inducing selective cerebral hypothermia includes a ventricle cooling device, a central vascular heating device, and a control console that provides a cooling means for said ventricle cooling device and a heating means for said central vascular heating device and a means to control said cooling and said heating. In accordance with another aspect of this invention, apparatus for inducing selective cerebral hypothermia includes a ventricle cooling balloon catheter that is constructed such that when the balloon is inflated within a lateral ventricle, the balloon conforms to the shape of the lateral ventricle without substantially inducing compressive ischemia within the brain tissue surrounding said lateral ventricle. In accordance with another aspect of this invention, apparatus for inducing selective cerebral hypothermia includes a ventricle cooling balloon catheter that is constructed such that when the balloon is inflated within a lateral ventricle the surface of the balloon substantially maintains intimate contact with the walls of said lateral ventricle between the Inferior Horn of said lateral ventricle and the Anterior Horn of said lateral ventricle. In accordance with another aspect of this invention, apparatus for inducing selective cerebral hypothermia includes a ventricle cooling balloon catheter constructed to be inserted into a lateral ventricle where the catheter enters the lateral ventricle in the vicinity of the Anterior Horn of said lateral ventricle and where the distal end of said balloon catheter may then be advance from vicinity of said Anterior Horn to the Inferior Horn of said lateral ventricle, and may due so in a normal ventricle or in a lateral ventricle that is compressed due to brain swelling.

OBJECTS AND ADVANTAGES

Accordingly, besides the objects and advantages of the method and apparatus to induce selective cerebral hypothermia to prevent secondary brain injury described in my patent above, several objects and advantages of the present invention are:

(a) to provide selective cerebral hypothermia to a brain at risk of secondary injury to the degree that offers maximum clinical benefit without inducing hypothermia in the rest of the body;

(b) to provide cerebral hypothermia to a brain at risk of secondary injury where the method for inducing hypothermia takes advantage of the fact that the walls of a lateral ventricle can be cooled by a balloon catheter, and brain tissue surrounding said ventricle may be cooled by heat conduction into the walls of said ventricle to the extent that prevents secondary injury.

(c) to provide selective cerebral hypothermia to a brain at risk of secondary injury within a minimal time after patient presentation where therapeutic temperatures are achieved rapidly due to the fact that only the brain is cooled;

(d) to provide selective cerebral hypothermia to a brain at risk of secondary injury where the degree of hypothermia is adjusted according to the physiological response to hypothermia, where the physiological response to hypothermia is a change in intra-cranial pressure;

(e) to provide selective cerebral hypothermia to a brain at risk of secondary injury where the degree of hypothermia is adjusted according to the physiological response to hypothermia, where the physiological response to hypothermia is a change in patient symptoms.

(f) to provide selective cerebral hypothermia to a brain at risk of secondary injury where the degree of hypothermia is adjusted according to the physiological response to hypothermia, where the physiological response to hypothermia is a change in localized blood perfusion;

(g) to provide selective cerebral hypothermia to a brain at risk of secondary injury where the degree of hypothermia is adjusted according to the physiological response to hypothermia, where the physiological response to hypothermia is a change in the size of the volume of infarcted tissue;

(h) to provide selective cerebral hypothermia to a brain at risk of secondary injury where the degree of hypothermia is adjusted according to the physiological response to hypothermia, where the physiological response to hypothermia is a change in blood chemistry.

(i) to provide apparatus for inducing selective cerebral hypothermia to a brain tissue at risk of secondary injury according to the objectives stated above;

(j) to provide a brain cooling system that consists of a ventricle cooling balloon catheter constructed for use in a lateral ventricle, a heating catheter for use in the central vascular system, and a control console;

(k) to provide a brain cooling system that is constructed to directly cool the walls of a lateral ventricle of the brain;

(l) to provide a cooling balloon catheter that is constructed to be placed into a lateral ventricle of the brain using well known surgical methods;

(m) to provide a brain cooling system that is constructed to provide for long term cooling and indwelling;

(n) to provide a brain cooling system that is constructed to provide for a means to sense a response to cooling;

(o) to provide a brain cooling system that is constructed to provide for a means to control the degree of cooling applied to the surrounding brain tissue.

DESCRIPTION—FIGS. 1–4—PREFERRED OPERATIONAL EMBODIMENTS

Figure 1A:
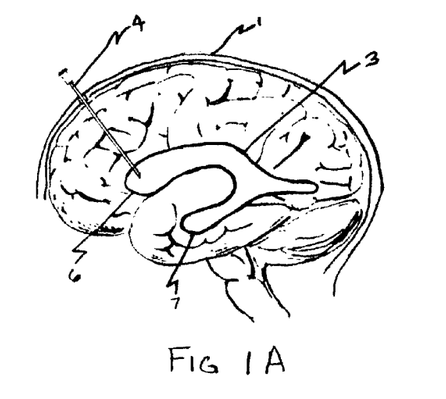
FIG. 1A through FIG. 1E depict a sagittal section of the human head and the placement of the cooling balloon catheter into a lateral ventricle of the brain.
Figure 1B:
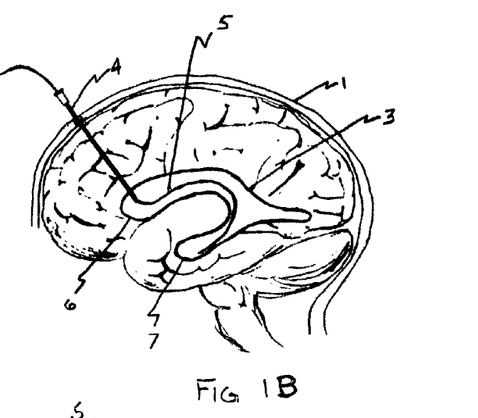
Figure 1C:
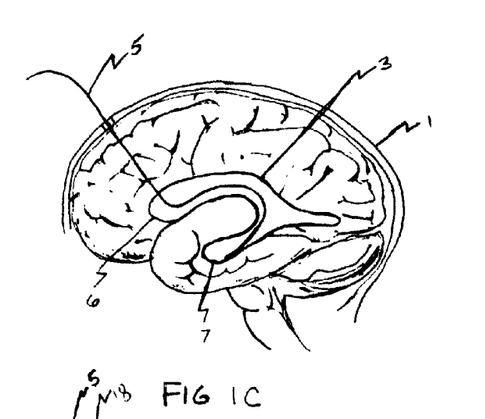
Figure 1D:
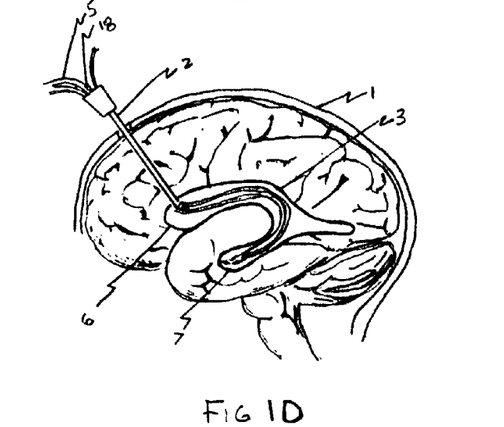
Figure 1E:
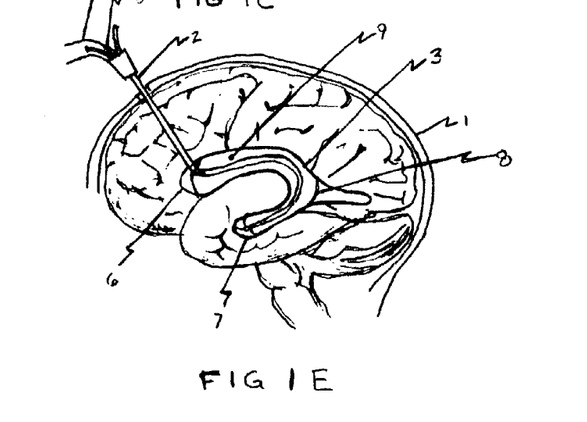

FIGS. 1A through 1B depict a sagittal section of a human head 1 and the placement of the cooling balloon catheter 2 into a lateral ventricle of the brain 3. FIG. 1A depicts the placement of ventricle access needle 4 by standard ventriculostomy means. FIG. 1B depicts a guide wire 5 placed into lateral ventricle 3 through ventricle access needle 4 where the guide wire enters the Anterior Horn 6 of the ventricle 3 as shown with the distal tip of the guide wire placed into the Inferior Horn 7 of lateral ventricle 3. Fluoroscopic guidance would normally be used to place guide wire 5 into lateral ventricle 3. FIG. 1C depicts the guide wire 5 in operational position after ventricle access needle 4 is removed. FIG. 1D depicts the cooling balloon catheter 2 in operational position after being slid over the guide wire 5. The cerebrospinal fluid is aspirated from the lateral ventricle trough the guide wire lumen 18. FIG. 1E depicts the cooling balloon catheter 2 in operation where catheter balloon 8 is inflated by cooling fluid 9 circulating within the catheter balloon 8. Note: FIG. 1 depicts a normal lateral ventricle, however, in brains which are swollen the lateral ventricle may compressed and contain little or no cerebrospinal fluid. Using a guide wire to access the Inferior Horn from entry in the vicinity of the Anterior Horn facilitates placement of the cooling balloon catheter in a compressed ventricle.

Figure 2:
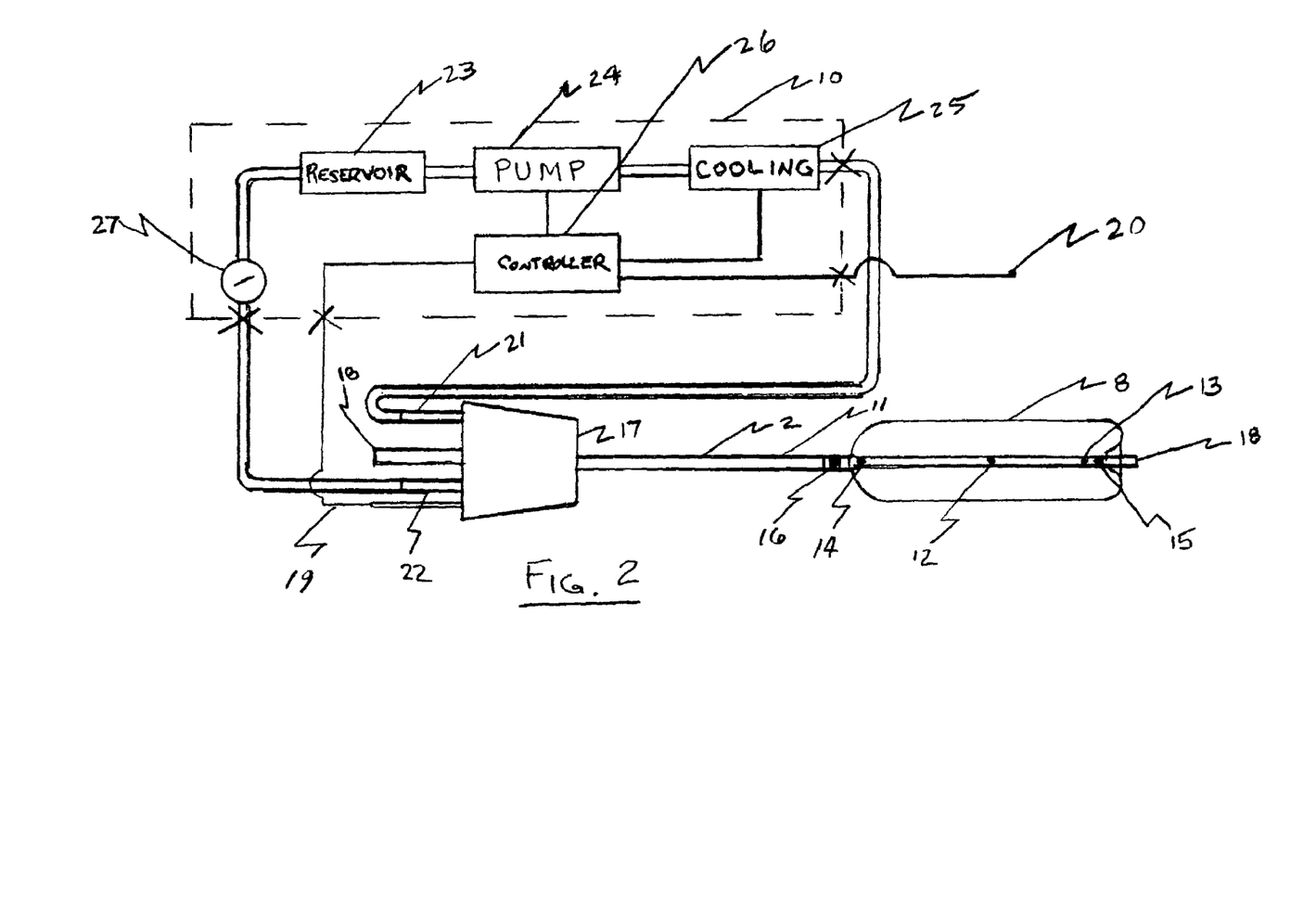
FIG. 2 depicts in schematic form the cooling balloon catheter and system console.

FIG. 2 depicts in schematic form an embodiment of the system showing the functional components of the control console 10, the cooling balloon catheter 2, intracranial temperature sensor 20, and the interconnects between the control console 10 and the cooling balloon catheter 2. The functional components of the cooling balloon catheter 2 are: elastic balloon 8, catheter shaft 11, temperature sensor 12, fluid inlet 13, fluid outlet 14, distal radiopaque marker 15, proximal radiopaque marker 16, proximal hub 17, guide wire lumen 18, temperature sensor cable 19, cooling fluid inlet tube 21, and cooling fluid outlet tube 22. The functional components of the control console 10 are: cooling fluid reservoir 23, cooling fluid pump 24, fluid cooler 25, system controller 26, and pressure regulator 27. Ventricle cooling is accomplished by pumping fluid, preferably saline at a temperature between 0 degrees centigrade and 37 degrees centigrade through elastic balloon 8 mounted on the distal end of cooling balloon catheter 2. Cooling fluid is supplied to the cooling balloon catheter 2 by system console 10 in a closed loop fashion. Pump 24 pumps cooling fluid from reservoir 23 through fluid cooler 25 into cooling balloon catheter 2 through cooling fluid inlet tube 21. Cooling fluid traverses catheter shaft 11 and enters elastic balloon 8 through fluid inlet 13 and exits elastic balloon 8 at fluid outlet 14 and then traverses catheter shaft 11 and exits cooling balloon catheter through cooling fluid outlet tube 22 and is returned to reservoir 23. Cooling fluid is pumped into elastic balloon 8 at a constant flow rate between 0.1 liters per minute and 1.0 liters per minute. Pressure regulator 27 maintains pressure within the elastic balloon 8. Pressure within elastic balloon 8 is maintained to the minimum value that overcomes the elastic energy within the walls of the balloon so that the balloon expands sufficiently to make intimate contact with the walls of lateral ventricle 3 without dilating lateral ventricle 3 and causing compressive ischemia in brain tissue surrounding lateral ventricle 3. The pressure required to expand elastic balloon 8 is dependent on the balloon material selected and its construction but should be between 10 mmHg and 100 mmHg. Temperature within the elastic balloon 8 is sensed by temperature sensor 12, which is mounted on the surface of catheter shaft 11 under elastic balloon 8. Signals from temperature sensor 12 are sent to system controller 26 via electrical leads 19. System controller 26 adjusts an output of pump 24, and/or the heat removal power of fluid cooler 25 to maintain desired temperature of the cooling fluid within the elastic balloon 8. Intracranial temperature sensor 20 may be optionally used to control the temperature of the cooling fluid in elastic balloon 8, or may be used to monitor intracranial temperature. Distal radiopaque marker 15, and proximal radiopaque marker 16 provide positional indication for fluoroscopic guidance. Guide wire lumen 18 provides for placement of cooling balloon catheter 2 into a lateral ventricle using a guide wire and also provides for aspiration of cerebrospinal fluid from the lateral ventricle by means of luer fitting (not shown) at the proximal end of the lumen 18. Note: FIG. 2 depicts the elastic balloon 8 pressurized and inflated. Elastic balloon 8 will be normally collapsed about catheter shaft 11 when not pressurized.

Figure 3:
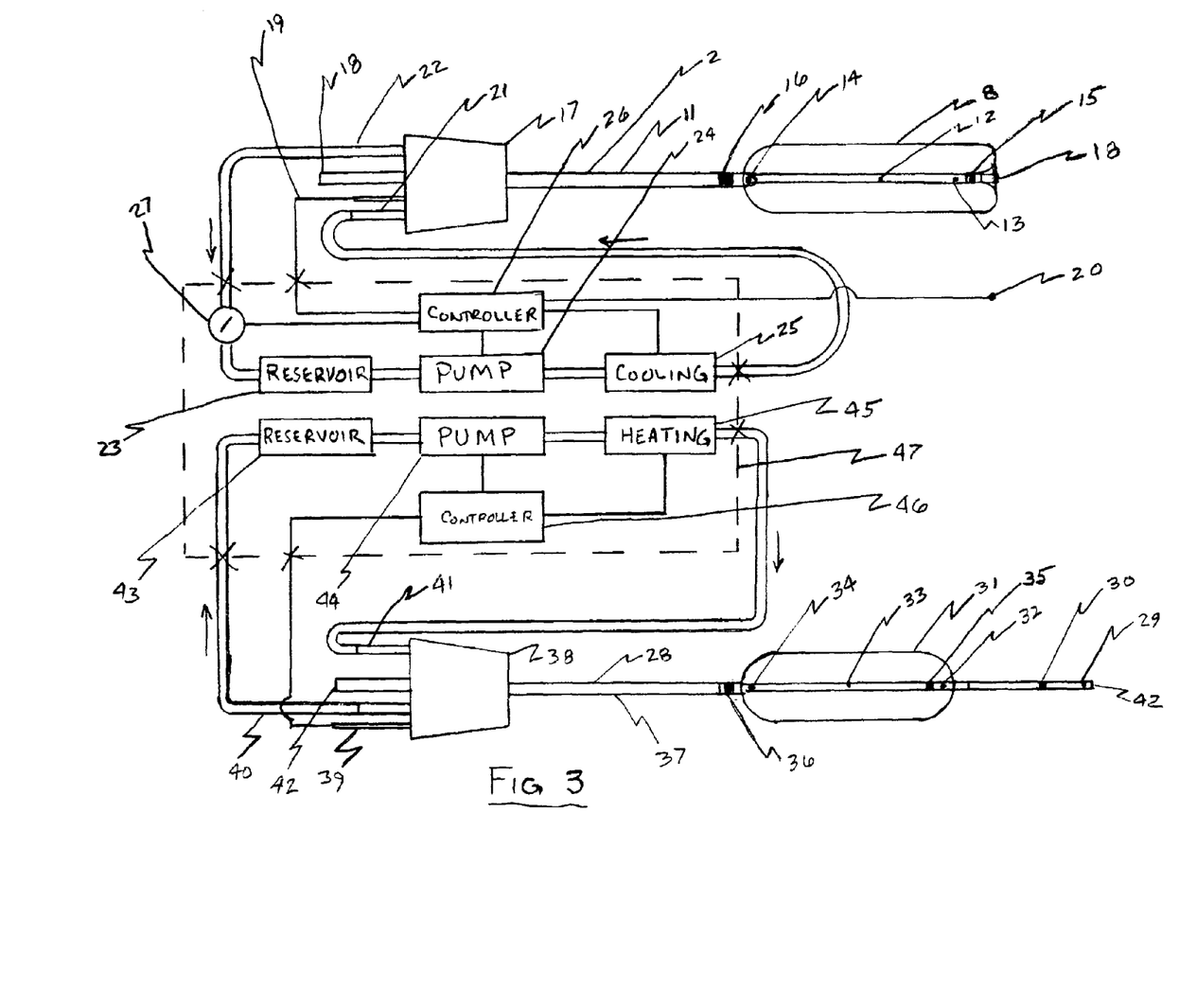
FIG. 3 depicts in schematic form an embodiment of the system showing a cooling balloon catheter, and a heating balloon catheter.

FIG. 3 depicts the selective cerebral hypothermia system that includes the ventricle cooling system as previously described with the addition of a means for warming the body core to replace body heat removed by cerebral ventricle cooling in order to maintain normal body temperature during cerebral hypothermia. This embodiment includes a warming balloon catheter 28 which is placed into the inferior vena cava and heats the blood within the vena cava to provide body core warming. In this embodiment the control console 47 contains a means for providing cooling fluid to cooling balloon catheter 2, and a means to provide warming fluid to warming balloon catheter 28, as well as a means to control said cooling and said warming. (Note: The cerebral cooling function and mechanisms were previously described, therefore the following describes only the functionality and mechanisms for body core warming.) Body core warming is accomplished by warming balloon catheter 28 in integral operation with warming components within control console 47. The functional components of warming balloon catheter 28 are: right atrium temperature sensor 29, right atrium radiopaque marker 30, non-compliant balloon 31, fluid inlet 32, temperature sensor 33, fluid outlet 34, distal balloon radiopaque marker 35, proximal balloon radiopaque marker 36, catheter shaft 37, proximal hub 38, temperature sensor leads 39, fluid outlet tube 40, fluid inlet tube 41 and guide wire lumen 42. The functional warming components within control console 47 are: fluid reservoir 43, pump 44, fluid warmer 45, and fluid warming controller 46. Body core warming is accomplished by pumping fluid, preferably saline at a temperature between 37 degrees centigrade and 50 degrees centigrade through non-compliant balloon 31 mounted near the distal end of warming balloon catheter 28. Warming fluid is supplied to the warming balloon catheter 28 by system control console 47 in a closed loop fashion. Pump 44 pumps warming fluid from reservoir 43 through fluid warmer 45 into warming balloon catheter 28 through warming inlet tube 41. Warming fluid traverses catheter shaft 37 and enters non-compliant balloon 31 through fluid inlet 32 and exits non-compliant balloon 31 at fluid outlet 34 and then transverses catheter shaft 37 and exits warming balloon catheter 28 through fluid outlet tube 40 and is returned to reservoir 43. Warming fluid is pumped into non-compliant balloon 31 at a constant pressure sufficient to fully expand non-compliant balloon 31. Warming fluid would normally be supplied at a pressure between 200 mmHg and 500 mmHg. The diameter of the non-compliant balloon is between 6 mm and 10 mm when fully inflated. The non-compliant balloon may be formed from PET polymer. The non-compliant balloon 31 transfers heat from the warming fluid within to blood flowing across the surface of non-compliant balloon 31. Therefore the diameter of the non-compliant balloon when fully inflated is by design significantly smaller then the blood vessel it resides in which in this embodiment is the inferior vena cava. The temperature within the non-compliant balloon is sensed by temperature sensor 33 mounted on the surface of catheter shaft 37. The objective of this invention is to provide cerebral hypothermia to degree that offers maximum clinical benefit while maintaining normal body core temperature. Since the brain is highly vascularized, when the brain is directly cooled as described by this invention, blood entering the brain is warmer than blood leaving the brain. Blood leaving the brain enters the right atrium of the heart though the superior vena cava. Blood is returned to the right atrium of the heart from the lower body through the inferior vena cava. By warming the blood entering the right atrium from the inferior vena cava in a controlled manner, the cooled blood returning from the brain and entering the right atrium from the superior vena cava will be mixed with the warmed blood such that the blood leaving the right atrium and entering the right ventricle will be at normal body temperature. This controlled mixing of warmed blood, and cooled blood is accomplished by positioning warming balloon catheter 28 into the inferior vena cave through femoral vein access such that the non-compliant balloon (warming mechanism) resides in the inferior vena cava and the distal tip of the warming balloon catheter 28 which contains right atrium temperature sensor 29 resides in the right atrium. Signals from right atrium temperature sensor 29 are sent to warming controller 46 via temperature sensor leads 39. The temperature of the fluid in the non-compliant balloon is adjusted by the warming controller to maintain normal body temperature (37 degrees centigrade) in the right atrium as sensed by right atrium temperature sensor 29. Warming balloon catheter is placed into operational position using standard endovasular catheter techniques. Radiopaque markers 30, 35, and 36 provide positional markers for fluoroscopic guidance.

Figure 4:
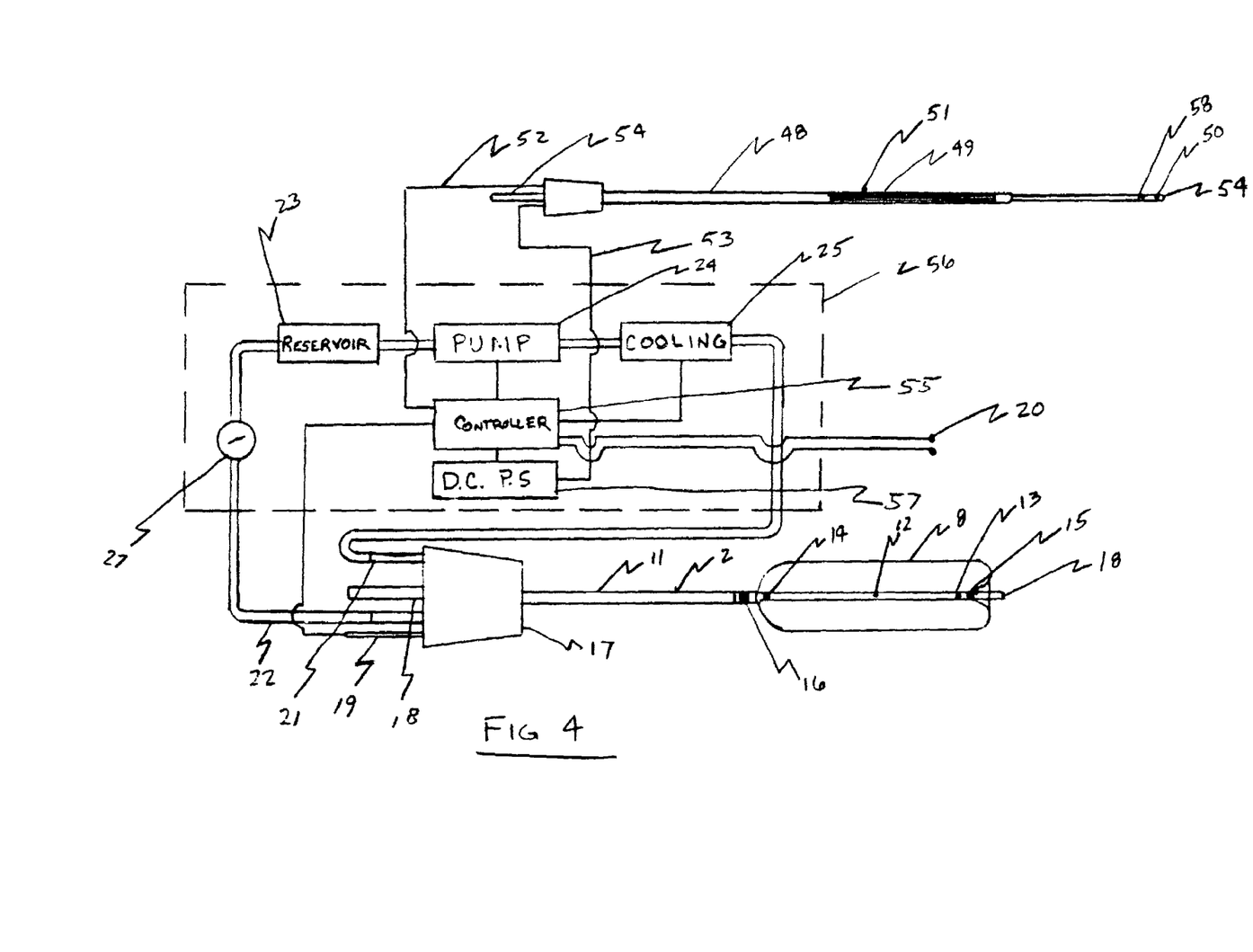
FIG. 4 depicts in schematic form an embodiment of the system showing a cooling balloon catheter and an electrically actuated heating catheter.

FIG. 4 depicts the selective cerebral hypothermia system as described in the paragraph above except that body core warming is accomplished with an electrically powered warming catheter 48 instead of warming balloon catheter 28. Function of warming catheter 48 is identical to the function of warming balloon catheter 28. In this embodiment, electrical warming element 49 of warming catheter 48 replaces the warming function of non-compliant balloon 31 of warming balloon catheter 28 as described above. Power is supplied to electrical warming element 49 from warming element power supply 57 of control console 56 via electrical warming element power leads 53. Power to warming element 49 is controlled by system controller 55. Temperature of the surface of the electrical warming element is sensed by temperature sensor 51 mounted on the surface of electrical warming element 49. Signals from temperature sensor 51, and right atrium temperature sensor 50 are sent to system controller 55 of control console 56. Temperature of the surface of warming element 49 is maintained between 37 degrees centigrade and 50 degrees centigrade by system controller 55 to maintain right atrium blood temperature at 37 degrees centigrade as sensed by right atrium temperature 50. Right atrium radiopaque marker 58 is used to guide placement of the distal tip of warming catheter 48 in the right atrium using fluoroscopy.

Figure 5:
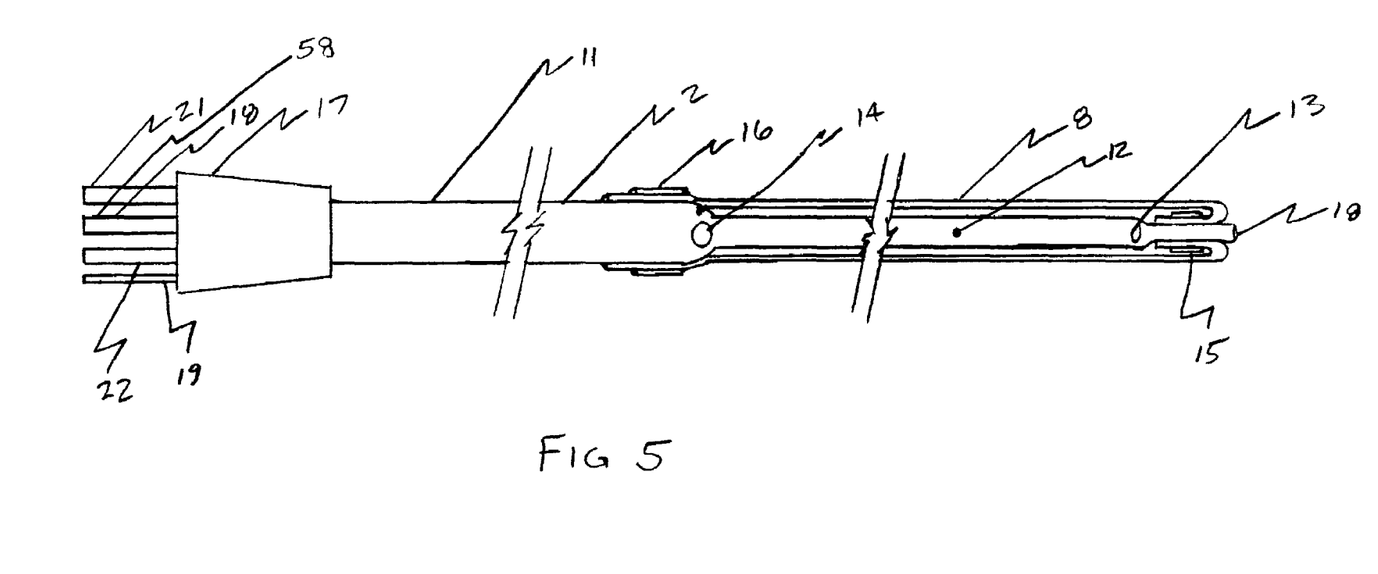
FIG. 5 depicts the construction of the cooling balloon catheter.
Figure 6A:
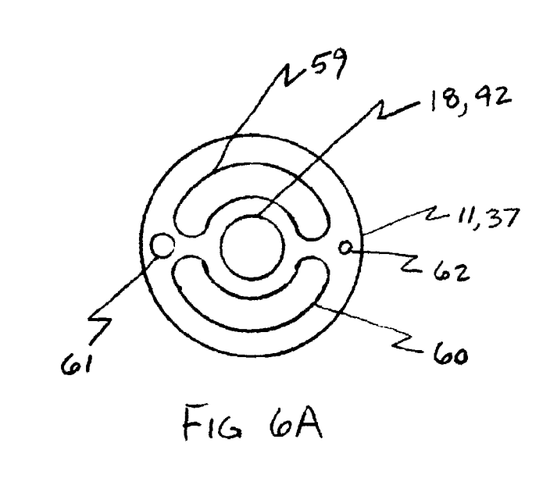
FIGS. 6A through 6C depict sectional views of the cooling balloon catheter shaft.
Figure 6B:
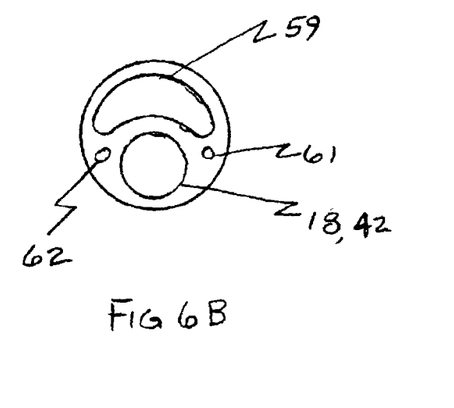
Figure 6C:
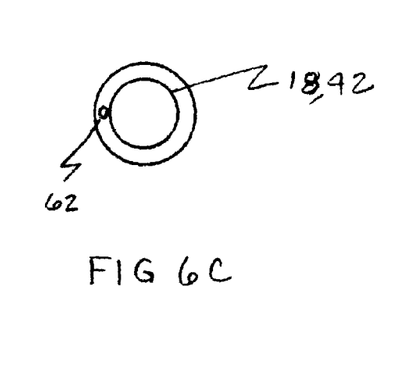

DESCRIPTION—FIGS. 5–7 PREFERRED CONSTRUCTION DETAILS

FIG. 5 depicts the construction of the cooling balloon catheter 2. Catheter shaft 11 is made of a medical grade thermoplastic material such as nylon. Catheter shaft 11 consists of three sections (see FIG. 6). Catheter shaft 11 has a guide wire lumen that traverses the catheter from the proximal end to the distal end and can accommodate standard guide wires from 0.010 to 0.032 inches in diameter. Catheter shaft 11 has two lumens for cooling fluid circulation and a separate lumen for the leads of temperature sensor 12. Proximal hub 17 provides communication with lumens in catheter shaft 11. Inlet tube 21, guide wire tube 58, and outlet tube 22 are standard medical luer fitting tubes. Temperature sensor leads are sheathed and terminated with a standard electrical connector (not shown) for removable connection to a control console 10, 47, or 56. Proximal hub 17 is formed by standard insert molding technique. Elastic balloon 8 is a medical grade silicone rubber tube with a wall thickness between 0.006 and 0.010 inches. It has a Shore A durometer of between 20 and 25, with an elongation rating between 800 and 1100%. Elastic balloon 8 is bonded to catheter shaft 11 with RTV adhesive with the adhesive joint reinforced by radiopaque markers 15 & 16 as shown. Fluid inlet 13 and fluid outlet 14 are formed by skiving catheter shaft 11 to access respective fluid lumens. The length elastic balloon 8 is between 5 and 10 cm long.

FIG. 6 depicts cross sections of cooling balloon catheter shaft 11, and warming balloon catheter shaft 37. Construction of both catheters is very similar. FIG. 6A shows section of catheter shaft 11 & 37 proximal to balloons 8 and 31 showing fluid inlet lumen 59, fluid outlet lumen 60, temperature sensor (under balloon) lead lumen 61, and right atrium temperature sensor lead lumen 62 (warming balloon catheter 28 only), and guide wire lumen 18 & 42. FIG. 6B shows a section of catheter shaft 11 & 37 under balloon 8 & 31 showing fluid inlet lumen 59, guide wire lumen 18 & 42, temperature sensor lead lumen 61, and right atrium temperature sensor lead lumen 62. FIG. 6C shows a section of catheter shaft 11 & 37 distal to balloons 8 & 31 showing guide wire lumen 18 & 42, and right atrium temperature sensor lead lumen 62. The three sections of the catheter shaft are thermally welded together to form the integral catheter shaft by standard means.

ALTERNATE EMBODIMENTS

Cooling of the brain may be accomplished by withdrawing cerebrospinal fluid from one or more ventricles, cooling the cerebrospinal fluid ex vivo and reintroducing the cooled cerebrospinal fluid back in the ventricle in a continuous or cyclical cycle. The cerebral spinal fluid within one or more ventricles of the brain may be cooled by placing a cooling probe into one or more ventricles where cerebrospinal fluid is cooled by free convection. The brain may be cooled by other means.

ADVANTAGES

From the description above there are a number of advantages my method and apparatus for inducing selective cerebral hypothermia for the prevention of secondary brain injury provide:
(a) The therapeutic agent (hypothermia) for preventing secondary injury according to this invention is applied directly to the brain.
(b) The therapeutic agent (hypothermia) for preventing secondary injury according to this invention is limited to the brain.
(c) Lower hypothermic temperatures can be practically achieved in the brain than can be achieved by the methods currently described in the art since only the brain is exposed to hypothermia.
(d) Lower hypothermic temperatures can be achieved in the brain than with methods described in the art.
(e) Hypothermic temperatures can be maintained longer in the brain than with methods described in the art.
(f) The degree of hypothermia in the brain can be adjusted according to the physiological response to hypothermia.
(g) Core body temperature may be precisely maintained at normal during cerebral hypothermia.

I claim:

1. A method for inducing cerebral hypothermia, comprising the steps of:
(a) placing a flexible elongated structure into a lateral ventricle of the brain whereby said elongated structure comprises a distal end and a proximal end, a fluid inlet port and a fluid outlet port whereby said fluid inlet port and said fluid outlet port are located in the vicinity of said distal end, a first fluid conduit between said fluid inlet port and said proximal end, and a second fluid conduit between said fluid outlet port and said proximal end;
(b) positioning said elongated structure within said lateral ventricle such that one of said fluid ports is located within said lateral ventricle in the vicinity of an anterior born of said lateral ventricle, and the second of said fluid ports is located within said lateral ventricle in the vicinity of a posterior horn of said lateral ventricle;
(c) connecting said proximal end of said elongated structure to a control console whereby said control console includes a means for circulating fluid and a means for cooling said fluid; and
(d) activating said control console thereby causing a flow of cooled fluid between said fluid outlet port and said fluid inlet port within said lateral ventricle thereby cooling the brain.

2. The method of claim 1 wherein an elastic balloon is mounted on said elongated structure in the vicinity of said distal end whereby said flow of said cooling fluid between said fluid outlet port and said fluid inlet port is contained within the walls of said elastic balloon.

3. The method of claim 2 wherein said elongated structure includes a third fluid port in the vicinity of said distal end proximal to said elastic balloon or distal to said elastic balloon, and a third fluid conduit connecting said third fluid port to said proximal end whereby said third fluid port and said third fluid conduit provide a means for removing cerebrospinal fluid from said lateral ventricle.

4. The method of claim 2 wherein pressure resulting from said fluid flow within said elastic balloon causes said elastic balloon to inflate such that the walls of said elastic balloon are substantially in intimate contact with the walls of said lateral ventricle.

5. The method of claim 1 wherein said elongated structure is a catheter constructed for placement into a ventricle of the brain substantially by standard ventriculostomy technique.

6. A method for inducing selective cerebral hypothermia comprising the steps of:
(a) placing a bran cooling device into a ventricle of the brain;
(b) applying a body heating device to the body;
(c) connecting said brain cooling device and said body heating device to a control console whereby said control console provides a means for cooling for said brain cooling device and a means for controlling said brain cooling, and also provides a means for heating for said body heating device and a means for controlling said body heating;
(d) activating said control console thereby cooling said brain with said brain cooling device while simultaneously heating said body with said body heating device.

7. The method of claim 6 wherein said brain cooling device comprises a catheter constructed for placement into a brain substantially by standard ventriculostomy technique.

8. The method of claim 6 wherein said body heating device comprises a catheter constructed to be placed into the central venous system by standard surgical technique.

9. The method of claim 6 wherein said brain cooling comprises circulation of cold fluid within a ventricle of the brain, whereby, said circulation is substantially limited to said ventricle.

10. The method of claim 6 wherein said control console includes a means for the operator of said control console to independently select a brain temperature and a body temperature, whereby said control console further includes a means for control of said brain cooling and said body heating such that said brain temperature and said body temperature is maintained at said operator selected temperatures by said control console.

11. A system for inducing and maintaining selective cerebral hypothermia comprising:
(a) a brain cooling device, the brain cooling device configured to circulate fluid within at least one lateral ventricle of a brain, whereby said circulation is substantially limited to said lateral ventricle, wherein the brain cooling device comprises:
a catheter shaft defining a first cooling fluid lumen having a first port and a second cooling fluid lumen having a second port, the first port configured to orient in proximity to an anterior horn of the lateral ventricle of the brain and the second port configured to orient in proximity to a posterior horn of the lateral ventricle of the brain; and a balloon disposed at the distal end of the catheter shaft and oriented in fluid communication with the first port of the first cooling fluid lumen and the second port of the second cooling fluid lumen, the balloon configured to expand, via a cooling fluid carried by first cooling fluid lumen and the second cooling fluid lumen, and contact a ventricle wall of the lateral ventricle (b) a body heating device (c) a brain temperature sensor (d) a body temperature sensor (e) a control console, and (f) a means for connecting said brain cooling device, said body heating device, said brain temperature sensor and said body temperature sensor to said control console, and whereby said control console comprises a means for providing cooling for said brain cooling device, a means for providing heating for said body heating device, a means for controlling brain cooling by said brain cooling device according to signals received from said brain temperature sensor, and a means for controlling body heating by said body heating device according to signals received from said body temperature sensor.

12. The system of claim 11 wherein said brain cooling device comprises a catheter constructed for placement into a ventricle of the brain substantially by standard ventriculostomy technique.

13. The system of claim 1 wherein said brain cooling device comprises a ventricle catheter including a means for positioning said ventricle catheter within a ventricle by radiological guidance.

14. The system of claim 11 wherein said brain temperature sensor is an intracranial temperature sensor.

15. The system of claim 11 wherein said brain temperature sensor is an integral component said brain cooling device.

16. The system of claim 11 wherein said body heating device comprises a vascular catheter.

17. The system of claim 16 wherein said vascular catheter comprises a distal end and a proximal end, a heating mechanism located in the vicinity of said distal end, and a temperature sensor located distal to said heating mechanism at a device from said heating mechanism of about 5 to 30 centimeters.

18. The system of claim 11 wherein said control console provides the operator of said system a means for independently selecting a brain temperature, and a body temperature, and further provides said operator a means for selecting a period of time that said brain and said body is maintained at said selected temperatures.

19. The system of claim 11 wherein the brain cooling device comprises a catheter shaft defining an aspiration lumen configured to aspirate cerebrospinal fluid of the lateral ventricle.

20. The system of claim 11 wherein the body heating device comprises a warming catheter device configured to insert within a vascular system, the warming catheter device comprising:

a warming catheter shaft having a proximal end and a distal end, at least one warming fluid lumen defined by the warming catheter shaft, and a warming balloon disposed at the distal end of the warming catheter shaft and in fluid communication with the at least one warming fluid lumen, the warming balloon configured to expand, via a warming fluid carried by the at least one warming fluid lumen, and thermally communicate with blood flowing within a vascular system.

21. A cooling system comprising:

a cooling catheter device having:

a cooling catheter shaft having a proximal end and a distal end, the catheter shaft defining an aspiration lumen configured to aspirate cerebrospinal fluid of the brain ventricle, at least one cooling fluid lumen defined by the cooling catheter shaft, and a cooling balloon disposed at the distal end of the cooling catheter shaft and in fluid communication with the at least one cooling fluid lumen, the balloon configured to expand, via a cooling fluid carried by the at least one cooling fluid lumen, and contact a ventricle wall of a brain ventricle to provide thermal communication between the balloon and the ventricle wall;

a warming catheter device configured to inert within a vascular system of a body, and a control console in thermal communication with the cooling catheter device and the warming catheter device, the console configured:

(i) to provide cooling fluid to the cooling balloon, via the at least one cooling fluid lumen, and expand the cooling balloon to thermally contact a ventricle wall of a brain ventricle of the body, and (ii) to provide an increase in temperature of the warming catheter device to allow thermal communication between the warming catheter device and blood flowing within the vascular system of the body.

22. The cooling system of claim 21 wherein the cooling balloon comprises an elastic material configured to minimize dilation of the brain ventricle upon expansion of the balloon.

23. The cooling system of claim 21 further comprising a temperature sensor disposed on the distal end of the cater shaft.

24. A method for inducing selective hypothermia comprising:

inserting a cooling catheter device within a ventricle of a brain of a body, the cooling catheter device having:

a catheter shaft having a proximal end and a distal end, the catheter shaft defining an aspiration lumen configured to aspirate cerebrospinal fluid of the brain ventricle;

at least one cooling fluid lumen defied by the catheter shaft; and a balloon disposed at the distal end of the catheter shaft and in fluid communication with the at least one cooling fluid lumen, removing cerebrospinal fluid from the ventricle of the brain via the aspiration lumen; and expanding the balloon, via a cooling fluid carried by the at least one cooling fluid lumen, to contact a ventricle wall of a brain ventricle to form a thermal communication between the balloon and the ventricle wall of the ventricle.

25. The method of claim 24 further comprising:
inserting a warming catheter device within a vascular system of the body; and
warming blood flowing within the vascular system.

26. A system for inducing and maintaining selective cerebral hypothermia comprising:
(a) a brain cooling device, the brain cooling device configured to circulate fluid within at least one lateral ventricle of a brain, whereby said circulation is substantially limited to said lateral ventricle, wherein the brain cooling device comprises a catheter shaft defining an aspiration lumen configured to aspirate cerebrospinal fluid of the lateral ventricle
(b) a body heating device
(a) a brain temperature sensor
(d) a body temperature sensor
(e) a control console, and
(f) a means for connecting said brain cooling device, said body heating device, said brain temperature sensor and said body temperature sensor to said control console, and whereby said control console comprises a means for providing cooling for said brain cooling device, a means for providing heating for said body heating device, a means for controlling brain cooling by said brain cooling device according to signals received from said brain temperature sensor, and a means for controlling body heating by said body heating device according to signals received from said body temperature sensor.

* * * * *

UNITED STATES PATENT AND TRADEMARK OFFICE
CERTIFICATE OF CORRECTION

| | |
|---|---|
| PATENT NO. | : 7,144,418 B1 |
| APPLICATION NO. | : 10/285165 |
| DATED | : December 5, 2006 |
| INVENTOR(S) | : Charles D. Lennox |

It is certified that error appears in the above-identified patent and that said Letters Patent is hereby corrected as shown below:

Column 9, line 61, in claim 1, change "born" to --horn--.

Column 10, line 27, in claim 6, change "bran" to --brain--.

Column 11, line 33, in claim 13, change "claim 1" to --claim 11--.

Column 11, line 48, in claim 17, change "device" to --distance--.

Column 12, line 26, in claim 21, change "inert" to --insert--.

Column 12, line 56, in claim 24, change "defied" to --defined--.

Column 13, line 15, in claim 26, change "(a)" to --(c)--.

Signed and Sealed this

Twentieth Day of February, 2007

JON W. DUDAS
*Director of the United States Patent and Trademark Office*